US006685964B1

(12) United States Patent
Bartholomaeus et al.

(10) Patent No.: US 6,685,964 B1
(45) Date of Patent: Feb. 3, 2004

(54) OPIOID ANALGESICS WITH CONTROLLED ACTIVE SUBSTANCE RELEASE

(75) Inventors: Johannes Bartholomaeus, Aachen (DE); Juergen Betzing, Bonn (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/484,016

(22) Filed: Jan. 18, 2000

(30) Foreign Application Priority Data

Jan. 18, 1999 (DE) .......................... 199 01 687

(51) Int. Cl.⁷ .............................. A61K 9/14; A61K 9/16; A61K 9/20; A61K 9/48
(52) U.S. Cl. .................. 424/489; 424/490; 424/464; 424/497; 424/451; 424/495
(58) Field of Search ................ 424/446, 451, 424/489, 490, 495, 497

(56) References Cited

U.S. PATENT DOCUMENTS 4,716,041 A * 12/1987 Kjornaes et al.
5,095,151 A    3/1992 Guley et al. ............... 564/349
5,955,104 A *  9/1999 Momberger et al.

FOREIGN PATENT DOCUMENTS

DE    33 06 250      8/1984
EP    647 448 A1     4/1995

OTHER PUBLICATIONS

Cha et al., "A One–Week Subdermal Delivery System for L–Methadone Based on Biodegradable Microcapsules", *Journal of Controlled Release*, pp. 69–78, 1988.

Bauer et al., "Uberzogene Arzneiformen" Wissenschaftliche Verlagsgesellschaft mbH, Stuttgart (1998) pp. 69–114.

* cited by examiner

*Primary Examiner*—Thurman K. Page
*Assistant Examiner*—Amy E Pulliam
(74) *Attorney, Agent, or Firm*—Crowell & Moring LLP

(57) ABSTRACT

An orally administered preparation with controlled lease of an opioid analgesic in the form of crystals having particle size of 10 μm to 3 mm, preferably of 50 μm to 1 mm, which have at least one controlled release coating.

23 Claims, No Drawings

OPIOID ANALGESICS WITH CONTROLLED ACTIVE SUBSTANCE RELEASE

BACKGROUND OF THE INVENTION

The present invention relates to an orally administered pharmaceutical formulation from which an opioid, analgesic active substance is released in a controlled manner.

Many formulations of analgesic painkillers which provide controlled release of the active substance are known from the prior art.

EP-A-0647448 inter alia has already described an analgesically active preparation with delayed active substance release which consists of a plurality of substrates containing opioid in controlled release form having a diameter of 0.1 to 3 mm as a single daily dose. Substrates suitable for this purpose may assume the form of spheroids, microbeads, pellets or granules. The production of this type of substrate entails relatively elaborate formulation methods, such as for example layer accretion agglomeration processes for pellets or the extrusion/spheronisation process for spheroids.

On the other hand, many opioid active substances occur in crystalline form when they are produced, such that there is a requirement to use them directly, i.e. without the aforementioned, elaborate formulation methods during pharmaceutical production.

SUMMARY OF THE INVENTION

The object of the present invention was accordingly to provide an orally administered preparation with controlled release of at least one opioid active substance, in which the crystals obtained during production of the active substance may be used directly, i.e. without elaborate formulation steps.

This object is achieved according to the invention by the provision of an orally administered preparation with controlled release of an opioid analgesic in the form of crystals having a particle size of 10 μm to 3 mm which have at least one controlled release coating. The crystals preferably have a particle size of 50 μm to 1 mm.

The preparations according to the invention contain at least one opioid in crystalline form as the analgesic active substance. Opioids which may be used include hydromorphone, oxycodone, morphine, levorphanol, methadone, dihydrocodeine, codeine, dihydromorphine, pethidine, fentanyl, piritramide, buprenorphine, tilidine, tramadol, the particular salts thereof or mixtures thereof. Tramadol, tramadol hydrochloride, morphine, morphine hydrochloride and/or morphine sulfate are very particularly preferred as the analgesic. The active substance crystals of the preparations according to the invention may be monocrystals or have a polycrystalline structure.

Apart from the stated opioid analgesics, the preparation according to the invention may contain non-opioid analgesics which optionally exhibit a synergistic action with the opioid analgesics. These non-opioid analgesics include ibuprofen, ketoprofen, flurbiprofen, propyphenazone, paracetamol, naproxen, acematacin, acetylsalicylic acid, metamizol and the salts thereof, preferably in crystal form.

The preparations used according to the invention are distinguished by controlled, preferably delayed, release of the analgesic. This is achieved by providing the active substance crystals with at least one controlled release coating. This coating ensures that the active substance is released in a controlled, delayed manner over the desired period of time. In this manner, it is possible purposefully to control the duration of action in comparison with conventional dosage forms, i.e. those without a controlled release coating. The release of the active substance is preferably adjusted in such a manner that the preparation need be administered at most twice, preferably only once, daily.

Suitable coating materials include any pharmaceutically safe coating materials which are known to persons skilled in the art. Natural, optionally modified, or synthetic polymers are preferably used as coating materials. These are polymers, such as for example cellulose ethers or acrylic resins. Water-insoluble or water-swellable cellulose derivatives, such as alkylcellulose, preferably ethylcellulose, or water-insoluble acrylic resins, such as poly(meth)acrylic acid and/or the derivatives thereof, such as the salts, amides or esters thereof, are very particularly preferred. These materials are known from the prior art, for example Bauer, Lehmann, Osterwald, Rothgang "Überzogene Arzneiformen", Wissenschaftliche Verlagsgesellschaft mbH, Stuttgart, 1998, pages 69 et seq., and are hereby incorporated by reference.

In addition to the water-insoluble polymers and waxes, it is optionally possible to adjust the active substance release rate by preferably also using up to 30 wt.% of non-controlled release, preferably water-soluble polymers, such as for example polyvinylpyrrolidone or water-soluble cellulose derivatives, such as hydroxyethylcellulose, hydroxypropylmethylcellulose or hydroxypropylcellulose, and/or known plasticisers.

In addition to the controlled release coating, the active substance crystals may also be provided with further coatings. Such a coating of a material other than the controlled release coating material may, for example, be applied onto the crystal surface as a non-controlled release interlayer. Coating materials preferably considered for this interlayer are cellulose ethers, polyvidones, polyacrylates or also natural polymers.

It is also possible to make the further coating, preferably over the controlled release coating, from the active substance of the crystals or from a preferably opioid analgesic differing from said active substance, from which coating this active substance is released in a non-controlled manner after oral administration. By means of this multilayer coating, it is possible to provide an initial dose for primary alleviation of the pain very rapidly after administration of the preparation, wherein the level of the analgesic may be maintained by the subsequent delayed release of the active substance. Coating materials which may be considered for this purpose are pharmaceutically safe materials in combination with the initial active substance, such as for example cellulose ethers, polyvidones or polyacrylates. It is, however, also possible to provide another pharmaceutical active substance in the non-controlled release coating in addition to or instead of the active substance of the crystals or of the further, preferably opioid, analgesic differing therefrom.

Apart from the controlled release coating, the crystals may furthermore also additionally have coatings which dissolve in a pH-dependent manner. It is thus possible, for example, to ensure that at least a proportion of the crystals of a preparation passes undissolved through the gastric tract and is not released until it reaches the intestinal tract.

In another preferred embodiment of the invention, the preparations also contain, in addition to the active substance crystals provided with a controlled release coating and optionally further coatings, which ensure controlled release of the active substance, non-controlled release active substance crystals which are, however, provided with one or more of the stated non-controlled release coatings.

Production of the opioid active substance crystals is known. The crystals are obtained directly during the necessary purification of the active substance.

The active substance crystals obtained immediately on production, preferably after recrystallisation, are provided with coatings in accordance with conventional, known processes, such as for example by spraying with solutions, dispersions and/or emulsions or by powder application processes. Coacervation is also a suitable process. To this end, an interlayer is initially applied over the individual crystals by coating the active substance crystals after the final purification step, crystallization and drying by spraying them with a lacquer solution or preferably an aqueous coating dispersion. The controlled release coating is applied thereover, again by spraying with a coating dispersion and subsequent drying. The thickness of this coating may be varied in accordance with the release profile to be achieved. Where still further coatings are applied, they are preferably produced using the same method.

The present invention also provides the orally administered preparations according to the invention in the form of capsules, in which the active substance crystals are present with controlled release of the opioid analgesic in accordance with the individual duration of release and quantity of analgesic for release which are to be achieved. The quantity of active substance crystals in a capsule is preferably selected such that the dose is sufficient for administration twice, preferably once, daily. This controlled release formulation in capsules may also be obtained without elaborate formulation methods, as the coated active substance crystals need only be packaged in capsules. According to the invention, the active substance crystals may also be combined into dosage units in a vial or sachet or be metered volumetrically by means of a dispenser. It is possible to add conventional auxiliaries, such as extenders, lubricants or disintegration promoters.

The orally administered preparations according to the invention may furthermore assume tablet form, in which the coated active substance crystals, with or without addition of conventional tablet auxiliaries and additives, are compression molded to form a tablet in accordance with the individual duration of release and quantity of opioid analgesic for release which are to be achieved. In this case too, it is advantageous if the quantity of active substance crystals which constitute the tablet is selected such that the duration of release and quantity of analgesic for release which are to be achieved are sufficient for administration twice, preferably once, daily.

Tablets having a high proportion of auxiliaries are preferably produced, so that the coated active substance crystals are retained in individual form. When the tablets disintegrate rapidly, the crystals from which controlled release proceeds are released. The release profile of the controlled release active substance crystals is retained even when tablets are divided.

It is also possible to produce tablets with a small proportion of auxiliaries. In this case, the coated active substance crystals may aggregate with each other on compression, thereby forming an additional controlled release matrix. Such tablets no longer disintegrate spontaneously, such that there is a greater degree of delay in comparison with individually coated crystals.

The preparations according to the invention preferably have a total tramadol concentration, calculated as the hydrochloride salt, of 10 to 1000 mg, preferably of 50 to 800 mg.

DETAILED DESCRIPTION OF PREFERRED EMBODIMENTS

Example 1

Tramadol hydrochloride crystals having a polycrystalline structure with a particle size of 250 to 500 $\mu$m were used after the production and purification thereof without a further formulation step. The stated quantities of ethylcellulose relate to the dry weight after application of the aqueous dispersion.

| | Composition: | |
|---|---|---|
| Crystals of | Tramadol HCl | 1.000 kg |
| Coating of | Ethylcellulose (Aquacoat ™) | 0.200 kg |
| | Dibutyl sebacate | 0.050 kg |
| Total | | 1.250 kg |

The tramadol hydrochloride crystals were set in motion with heated air in a fluidized bed apparatus, and the aqueous ethylcellulose suspension, into which the dibutyl sebacate had previously been stirred, was slowly sprayed onto the crystals by means of a two-fluid nozzle. Once the suspension had been applied, the crystals were dried.

Example 2

The crystals coated according to Example 1 were processed to produce capsules. To this end, the coated crystals were mixed with the above-stated auxiliaries in a cube mixer and packaged in rigid size 2 gelatine capsules using a capsuling machine.

| | Composition: | |
|---|---|---|
| Capsule filling | per capsule | per batch |
| Tramadol HCl crystals, coated according to Example 1 | 125 mg | 1.25 kg |
| Microcrystalline cellulose | 75 mg | 0.75 kg |
| Sodium carboxymethyl starch, type A | 45 mg | 0.45 kg |
| Magnesium stearate | 5 mg | 0.05 kg |
| Total | 250 mg | 2.50 kg |

Example 3

250 g of the crystals coated according to Example 1 were mixed with 344 g of microcrystalline cellulose and 6 g of magnesium stearate and compression moulded to form rapidly disintegrating tablets of a diameter of 10 mm and a weight of 300 mg.

Example 4

Tramadol hydrochloride crystals having a polycrystalline structure with a particle size of 250 to 500 $\mu$m were used after the production and purification thereof. The details concerning the intermediate layer and the controlled release layer relate to dry weight after application of the aqueous dispersion.

The tramadol hydrochloride crystals were set in motion with heated air in a fluidized bed apparatus and the aqueous dispersion for producing the intermediate layer was sprayed on first and dried. Then, the ethylcellulose suspension, into which the dibutyl sebacate had previously been stirred, was slowly sprayed onto the crystals by means of a two-fluid nozzle. Once the suspension had been applied, the crystals were dried.

| Composition: | | |
|---|---|---|
| Crystals of | Tramadol HCl | 1.000 kg |
| Intermediate layer | Macrogol 6000 | 0.025 kg |
| | Talcum | 0.040 kg |
| | Hydroxypropylmethylcellulose, type 2910, 6 mPas | 0.100 kg |
| Coating of | Ethylcellulose (Aquacoat ™) | 0.200 kg |
| | Dibutyl sebacate | 0.050 kg |

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A preparation for oral administration with controlled release of an opioid analgesic comprising the opioid analgesic in the form of crystals having a crystal size of 10 μm to 3 mm, each of said crystals having at least one controlled release coating applied directly to the crystals, without an intervening formulation step.

2. An orally administered preparation according to claim 1, wherein said crystals have a crystal size of 50 μm to 1 mm.

3. An orally administered preparation according to claim 1, wherein the crystals are monocrystals or have a polycrystalline structure.

4. An orally administered preparation according to claim 1, wherein the controlled release coating is based on a polymer.

5. An orally administered preparation according to claim 4, wherein the controlled release coating contains a positive amount up to 30 wt.% of a non-controlled release polymer.

6. An orally administered preparation according to claim 4, wherein said controlled release coating comprises at least one polymer selected from the group consisting of acrylic resins and cellulose derivatives.

7. An orally administered preparation according to claim 6, wherein said controlled release coating comprises an alkylcellulose polymer.

8. An orally administered preparation according to claim 6, wherein said controlled release coating comprises ethylcellulose and/or poly(meth)acrylic acid and/or at least one derivative thereof.

9. An orally administered preparation according to claim 8, further comprising a positive amount up to 30 wt.% of hydroxypropylcellulose, hydroxymethylcellulose, hydroxypropylmethylcellulose or polyvidone.

10. An orally administered preparation according to claim 1, wherein said opioid analgesic is selected from the group consisting of hydromorphone, oxycodone, morphine, levorphanol, methadone, dihydrocodeine, codeine, dihydromorphine, pethidine, piritramide, fentanyl, tilidine, buprenorphine, tramadol, pharmaceutically acceptable salts thereof, and mixtures thereof.

11. An orally administered preparation according to claim 10, wherein the opioid analgesic comprises at least one substance selected from the group consisting of tramadol, tramadol hydrochloride, morphine, morphine hydrochloride and morphine sulfate.

12. An orally administered preparation according to claim 1, wherein the crystals have said controlled release coating and at least one further coating.

13. An orally administered preparation according to claim 12, wherein said further coating comprises a coating of a material other than the controlled release coating applied directly onto the crystal surface as a non-controlled release interlayer.

14. An orally administered preparation according to claim 12, wherein said further coating comprises a coating resistant to gastric juices.

15. An orally administered preparation according to claim 12, wherein said further coating comprises a pharmaceutically active substance.

16. An orally administered preparation according to claim 15, wherein said pharmaceutically active substance is an opioid analgesic.

17. An orally administered preparation according to claim 16, wherein the opioid analgesic in said further coating is the same as in said crystals.

18. An orally administered preparation according to claim 1, wherein the crystals are present in a capsule, a sachet, a vial, or a dispenser.

19. An orally administered preparation according to claim 18, wherein the crystals are present in a metering dispenser.

20. An orally administered preparation according to claim 1, wherein the crystals are compression molded to form tablets.

21. An orally administered preparation according to claim 20, wherein the crystals are compression molded with conventional auxiliaries and additives to form tablets.

22. An orally administered preparation according to claim 20, wherein the crystals are compression molded with non-controlled release pharmaceutical active substances to form tablets.

23. An orally administered preparation according to claim 1, comprising 10 to 1000 mg of tramadol, calculated as the hydrochloride salt.

* * * * *